United States Patent [19]

Gentry

[11] Patent Number: 5,516,955
[45] Date of Patent: May 14, 1996

[54] CATALYTIC DISTILLATION TO PRODUCE ORTHOXYLENE AND PARAXYLENE

[75] Inventor: Joseph C. Gentry, Houston, Tex.

[73] Assignee: Glitsch International, Inc., Dallas, Tex.

[21] Appl. No.: 220,313

[22] Filed: Mar. 30, 1994

[51] Int. Cl.$^6$ .................. C07C 5/22; C07C 7/00
[52] U.S. Cl. .............. 585/477; 585/480; 585/481; 585/800; 585/805
[58] Field of Search ................. 585/477, 800, 585/480, 481, 805

[56] References Cited

U.S. PATENT DOCUMENTS

| | | | |
|---|---|---|---|
| 2,403,672 | 7/1946 | Matuszak | 586/664 |
| 3,091,586 | 5/1963 | Pappas et al. | 208/210 |
| 3,629,478 | 12/1971 | Haunschild | 203/38 |
| 3,634,534 | 1/1972 | Haunschild | 203/28 |
| 3,770,841 | 11/1973 | Meyers, Jr. | 585/481 |
| 4,118,429 | 10/1978 | Fritsch et al. | 208/143 |
| 4,215,011 | 7/1980 | Smith, Jr. | 252/426 |
| 4,232,177 | 11/1980 | Smith, Jr. | 585/324 |
| 4,302,356 | 11/1981 | Smith, Jr. | 252/426 |
| 4,307,254 | 12/1981 | Smith, Jr. | 568/697 |
| 4,336,407 | 6/1982 | Smith, Jr. | 568/697 |
| 4,443,559 | 4/1984 | Smith, Jr. | 502/527 |
| 4,654,456 | 3/1987 | Nimry | 585/477 |
| 4,697,039 | 9/1987 | Schmidt | 585/477 |
| 4,783,568 | 11/1988 | Schmidt | 585/477 |
| 5,015,794 | 5/1991 | Reichmann | 585/258 |
| 5,177,283 | 1/1993 | Ward | 585/446 |
| 5,277,847 | 1/1994 | Gentry | 261/114.1 |

*Primary Examiner*—Sharon Gibson
*Attorney, Agent, or Firm*—Charles L. Willis

[57] ABSTRACT

An improvement to a known process in which $C_8$ aromatic hydrocarbons are treated to recover a desired isomer of xylene, and in particular o-xylene or p-xylene. A step in recovering isomers of xylene typically includes subjecting a mixture of xylenes to fractional distillation and drawing a stream rich in o-xylene from the fractionation column. The current improvement involves the steps of contacting the contents of the fractionation column with an isomerization catalyst, thereby isomerizing $C_8$ aromatic hydrocarbons in the fractionation column toward equilibrium and consequently enhancing the effectiveness of the fractional distillation in the recovery of the desired xylene isomer. The process can be carried out in the xylene splitter of existing apparatus by making appropriate modifications thereto. It also can be carried out in newly-designed and fabricated apparatus. Embodiments are disclosed for favoring the production either of o-xylene or p-xylene.

7 Claims, 3 Drawing Sheets

5,516,955

CATALYTIC DISTILLATION TO PRODUCE ORTHOXYLENE AND PARAXYLENE

BACKGROUND OF THE INVENTION

1. Field of the Invention

The invention relates to the processing of $C_8$ aromatic hydrocarbons to recover a desired isomer of xylene, and in particular to the recovery of o-xylene and p-xylene.

2. Discussion of the Background

Distillation columns are used to separate selected components from multicomponent streams by fractional distillation. It has been known that the presence of a catalyst in a distillation column can be useful in the production of various aliphatic hydrocarbons. This is particularly true of processing lighter aliphatic hydrocarbons.

U.S. Pat. No. 2,403,672 of Matuszak shows separating isobutylene from butene-1 in a combined isomerization reactor and fractional distillation column.

U.S. Pat. No. 3,634,534 of Haunschild discloses a process carried out in distillation columns having catalyst disposed in selected downcomers. The disclosure shows processing a $C_5$ refinery stream. It is described as being advantageously applied to the separation of nontertiary olefins from tertiary olefins.

My U.S. Pat. No. 5,277,847 of Gentry et al. discloses improved catalyst-downcomer-tray assemblies for vapor-liquid contact towers.

In contrast to technology such as shown in the patents of Matuszak and Haunschild, the production of heavier hydrocarbons and the isolation of desired isomers thereof has involved the use of structure and processes that are more complex and, importantly, more expensive. This has been particularly true in the recovery of aromatic hydrocarbons. Specific reference is made to processing streams having significant content of $C_8$ aromatic hydrocarbons and isolating o-xylene therefrom. Such streams may contain significant amounts of ethylbenzene, but not necessarily.

The production of specific xylene isomers is an important petrochemical process. Large quantities of p-xylene are consumed in processes leading to the production of polyesters used in clothing manufacture. O-xylene is used as a raw material in the production of phthalic anhydride which, in turn, is used for plasticizers, for alkyd resins, and for polyesters. Of the isomers of xylene, it is the p-xylene that is generally considered to be the most valuable and desired product. Not surprisingly, a process that values the recovery of o-xylene is also likely to be adapted to recovering p-xylene.

It is known to separate o-xylene from mixed xylenes by conventional distillation. The stream that is thus depleted of o-xylene typically is routed to a separate unit to separate and recover p-xylene. In the alternative, the p-xylene may be removed before the xylene distillation step. The result is a stream of $C_8$ aromatic hydrocarbons that is deficient in o-xylene and p-xylene, and richer in ethylbenzene and m-xylene.

In the current state of the art, there are two main classes of xylene isomerization reactions. In one class, all four of the $C_8$ aromatic isomers are isomerized toward an equilibrium mixture. In the other class, only the xylenes are isomerized toward an equilibrium mixture; the ethylbenzene is converted into benzene. Both classes of reaction yield approximately an equilibrium ratio of the xylene isomers, regardless of their ratio in the feed stream.

U.S. Pat. No. 3,770,841 of Meyers discloses a process for the recovery of p-xylene in which o-xylene or m-xylene or both may also be recovered as desired. The process includes subjecting a feed stream to an initial separation step, which may be a chromatographic or adsorption step, to recover p-xylene and remove ethylbenzene. Then in a series of fractional distillation columns, m-xylene and o-xylene are recovered as overheads and $C_{9+}$ is drawn off as a bottom. One of the overhead streams, which contains o-xylene and m-xylene, is passed to a reactor, where it undergoes catalytic isomerization to convert at least a portion of the stream to additional p-xylene. Preferably the isomerization is a low temperature isomerization carried out in the presence of a toluene diluent. The output of the reactor is fed to a distillation column, where the toluene is recovered along with any benzene that may be present. The bottoms are fed to an additional separation stage, which may be like the first, for the recovery of p-xylene. The output of that stage is fed to the above-mentioned series of fractional distillation columns.

U.S. Pat. Nos. 4,697,039 and 4,783,568 of Schmidt disclose processes for the production of a desired xylene isomer, preferably p-xylene. The feed stream enters at 1 and optionally at 33. Following a stage 2 for the separation of p-xylene, the stream passes through a xylene isomerization zone at 6, optional fractional distillation at 12, and a transalkylation zone 14 where dealkylation and isomerization occur. The output of zone 14 is fed to a series of fractional distillation columns where $C_6$, $C_7$, $C_8$, and $C_9$ streams, respectively, are drawn off as overhead. Column 29 is called a xylene column. In the embodiment shown in the drawing, the overhead of this column is fed into a p-xylene separation zone in the form of p-xylene recovery unit 2 to allow the recovery of p-xylene. In a disclosed variation (e.g., '039 patent, column 9, lines 48–51), the raffinate stream of the xylene separation zone is further fractionated to produce a stream rich in o-xylene.

Yet another example of prior art apparatus and process is shown in FIG. 1 herein. A feed stream 5 containing mixed xylenes is introduced typically at a location between the middle portion and the top of a xylene splitter column 10. As typical, the mixed xylene stream contains ethylbenzene. The stream may contain heavier and lighter hydrocarbons. The preferred location of the feed may change depending on its composition.

The stream enters a xylene splitter zone shown in the drawing in the form of fractional distillation towers 12 and 14. For economic reasons it is typical for this zone to be fabricated as two separate towers, as shown. If desired, they could be fabricated as one tower without significant alteration of their function. For purposes of the present disclosure, the two towers 12 and 14 collectively will be treated functionally as a single column 10. A typical xylene splitter may contain between seventy-five and one hundred fifty trays.

O-xylene is drawn off in the bottoms of the xylene splitter 10, together with $C_{9+}$. Typically more than ninety-five percent of the p-xylene and m-xylene will have been removed. If desired, these bottoms may be subjected to further distillation in an additional column, not shown in the drawing, for the recovery of the o-xylene from the $C_{9+}$.

The overhead of the xylene splitter 10, being enriched in p-xylene, is fed to a known p-xylene recovery unit 16, which may be of a type discussed in the patents noted above. Therein, p-xylene is recovered as a valuable product. Typically such units are sensitive to the p-xylene concentration in the feed. In this regard, the separation of p-xylene is aided by the prior removal of most of the o-xylene.

The output of the p-xylene recovery unit 16 will have been partially depleted of o-xylene and p-xylene. It is fed to an isomerization reactor 18 which contains a catalyst. Therein, the xylenes and ethylbenzene in the stream undergo catalytic isomerization to produce a stream that is closer to an equilibrium state for xylene isomers. One result of the isomerization step is that the output of the isomerization reactor will be enriched in p-xylene and o-xylene as compared with the feed to the isomerization reactor.

The output of the isomerization reactor is fed to a flash drum 20 for the removal of any $H_2$ or other gases that might have resulted from the cracking of ethylbenzene. The stream then is fed to a fractional distillation column 22 to distill overhead any benzene that may be present. Benzene is expected to be produced in small amounts by the cracking of ethylbenzene or xylenes during the isomerization reaction. The bottoms of column 22 are fed to another fractional distillation column 24, where toluene is recovered as an overhead. The bottoms of column 24 are mixed with the fresh feed 5 to the system and reintroduced to the xylene splitter 10.

The economic viability of any process for the production of xylenes is dependent on several factors. Among these are the total yield of the desired xylene isomer or isomers; the initial capital cost of the equipment such as columns, reactors and piping and the catalyst necessary for operating the process; and the cost of utilities. With specific reference to the recovery of o-xylene, the profitability of fabricating or operating a xylene splitter is further governed by the benefit that upstream o-xylene recovery confers on the p-xylene recovery step and by the relationship of the incremental energy cost of operating the xylene splitter to the price difference between o-xylene and mixed xylenes.

Given these known constraints and goals, the prior art discussed above nonetheless is characterized by the comparatively high capital cost of plural distillation columns disposed in a loop with an isomerization reactor and, typically, a p-xylene recovery unit. O-xylene recovery by fractional distillation, isomerization of the xylenes in the stream toward an equilibrium state, and p-xylene separation occur in discrete steps, sequentially, in separate units.

SUMMARY OF THE INVENTION

The current invention provides an economically attractive process for recovering a desired isomer of xylene and, in particular, o-xylene or p-xylene. When applied to a revamp or retrofit setting, the process can profitably improve the yield of o-xylene (and p-xylene) with appropriate capital and additional operating expenditures. When used in new construction, the process can provide a higher yield of o-xylene (and p-xylene) for a given capital and operating cost.

In one view, the invention shifts the equilibrium of the process of $C_8$ isomerization by removing o-xylene from the reactor in which the isomerization reaction occurs. This results directly in a net increase in o-xylene production over what is currently obtained by separate isomerization and distillation operations.

In another view, the invention provides a useful revamp of existing equipment by augmenting the existing isomerization reactor with an additional isomerization reaction that occurs in the xylene splitter. As above, this revamp permits a net increase in o-xylene or p-xylene production over the unimproved process.

According to a further aspect, the invention provides an improvement to a known process in which hydrocarbons including $C_8$ aromatic hydrocarbons are treated to recover at least a desired isomer of xylene, wherein the process comprises the steps of receiving a mixture that contains mixed xylenes into a fractionation column, subjecting the mixture to fractional distillation in the fractionation column, and drawing a stream rich in the desired isomer of xylene from the fractionation column. The improvement involves the steps of contacting the contents of the fractionation column with an isomerization catalyst, thereby isomerizing $C_8$ aromatic hydrocarbons in the fractionation column toward equilibrium and consequently enhancing the effectiveness of the fractional distillation in the recovery of o-xylene or p-xylene. This improved process can be carried out in the xylene splitter of existing apparatus by making appropriate modifications thereto. It also can be carried out in newly-designed and fabricated apparatus.

According to one version of the process, the isomerization catalyst is disposed at a single zone within the fractionation column, and the xylene mixture is received into the fractionation column at a location beneath the isomerization catalyst. This version of the process is used when one intends to favor the recovery of additional o-xylene at the bottom of the column by converting mixed xylenes in the column into additional o-xylene. Typically the zone of isomerization catalyst will be disposed within the upper half of the column.

According to another version of the process, the isomerization catalyst is disposed at a single zone within the fractionation column, and the mixture is received into the fractionation column at a location above (as opposed to beneath) the isomerization catalyst. This version of the process is used when one intends to favor the recovery of additional p-xylene near the top of the column by converting mixed xylenes in the column into additional p-xylene. Typically the zone of isomerization catalyst will be disposed within the lower half of the fractionation column.

According to yet another version of the process, the isomerization catalyst is disposed in two zones within the fractionation column, and the mixture is received into the fractionation column at a location between the two zones. In such a case, it may be desirable to subject the mixture to fractional distillation between the two zones of isomerization catalyst.

Various forms of isomerization catalysts have been known for many years. It is presently preferred to use a high activity catalyst. However, the choice of an appropriate catalyst will depend upon process conditions.

A number of isomerization systems exist having catalysts that may be suitable for the current invention. Among these are those available commercially under the trademarks MHTI, MLPI, Octafining-II, and Isomar. (MHTI, or Mobil High Temperature Isomerization, and MLPI, or Mobil Low Pressure Isomerization, are available from Mobil Research and Development Corporation of Princeton, N.J. Octafining-II is available from Acreon Catalysts of Houston, Tex., formally Engelhard Corporation. Isomar systems are available from UOP, Inc. of Des Plaines, Ill.)

BRIEF DESCRIPTION OF THE DRAWINGS

The brief description above, as well as further objects, features and advantage of the present invention will be more fully appreciated by reference to the following detailed description of presently preferred but nonetheless illustrative embodiments in accord with the present invention when taken in conjunction with the accompanying drawings wherein.

DESCRIPTION OF THE PREFERRED EMBODIMENTS

As has been said, the current invention in useful in both revamp and new construction settings. Candidate processes for improvement by revamp according to the current invention include those identified above in the Discussion of the Background. The investment cost to achieve incremental o-xylene capacity by such revamping may be lower than by any other means that is commercially available. An example of such a revamp will now be discussed with reference to FIG. 2.

Figure 1:
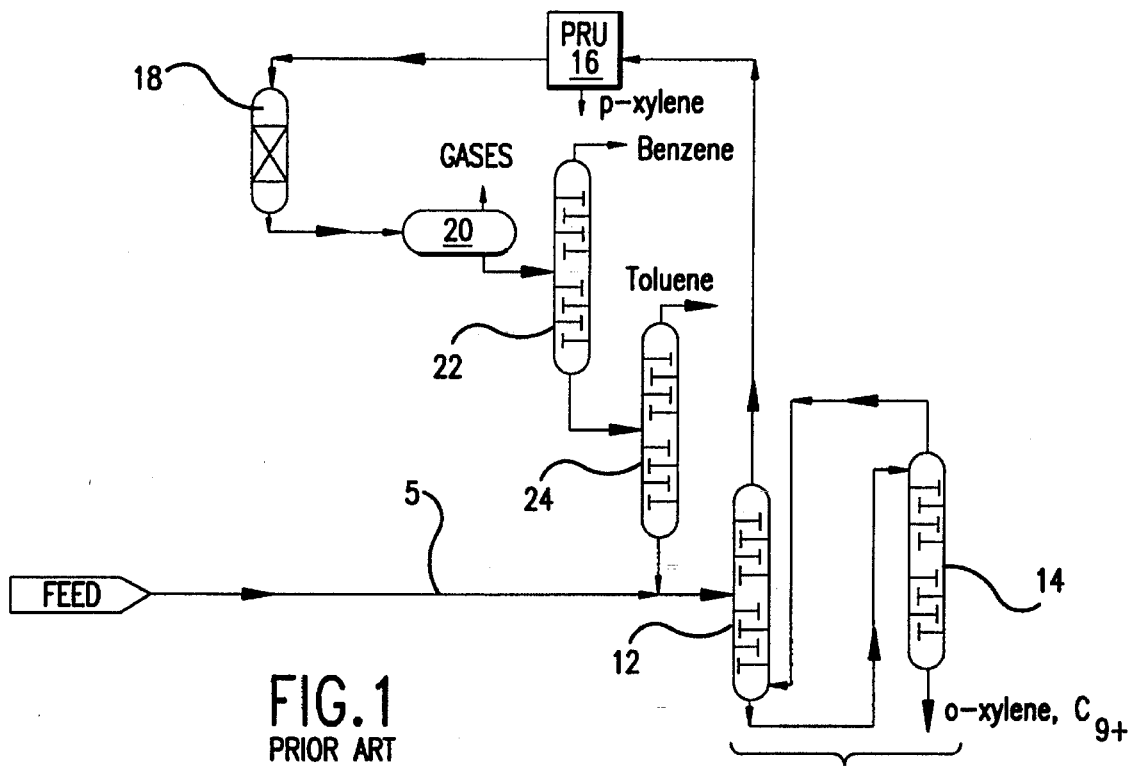
FIG. 1 shows an example of a typical known system for carrying out a known method of recovering o-xylene and p-xylene.
Figure 2:
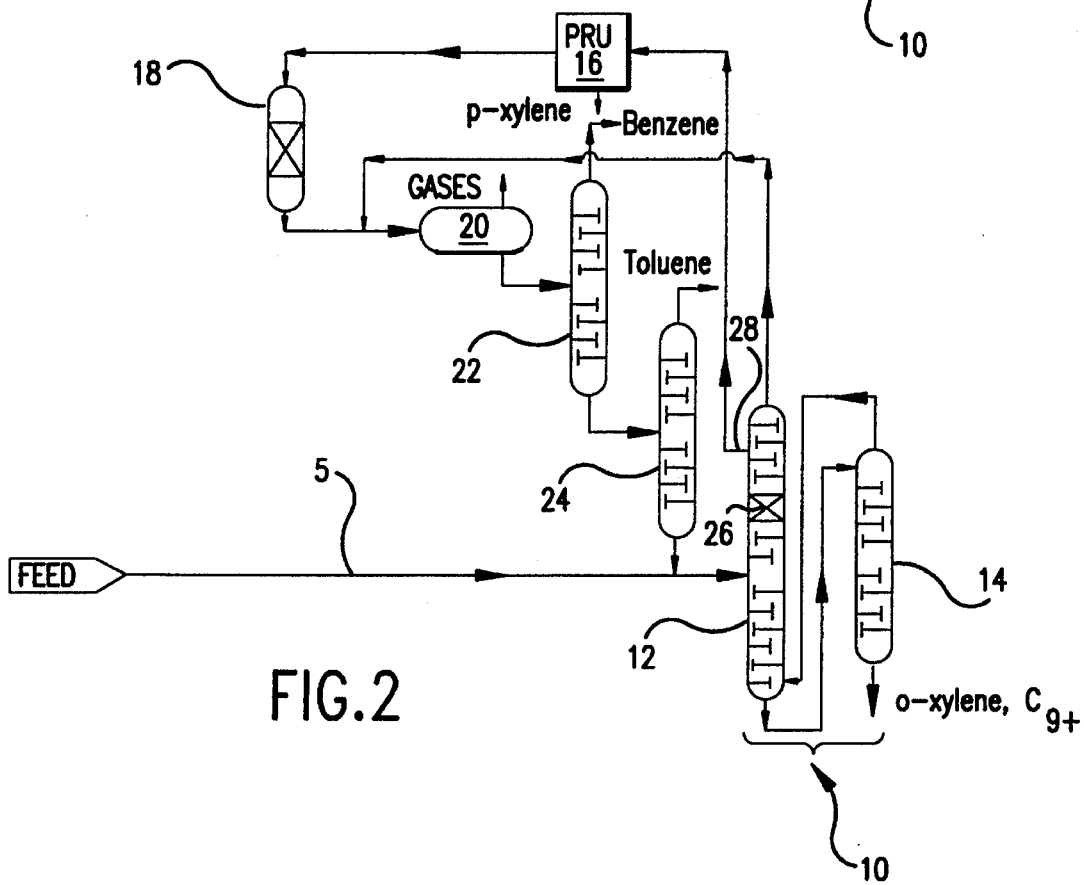
FIG. 2 shows the system of FIG. 1 economically retrofitted to carry out a method according to the current invention in which feed to a xylene splitter enters beneath a single zone of isomerization catalyst.

In FIG. 2, the structure and operation is as has been described with respect to FIG. 1, with the following exceptions. The xylene splitter 10 is provided with a single zone 26 of a catalyst effective to isomerize xylenes toward an equilibrium condition. The catalyst zone is located above the location of the feed to the xylene splitter. This arrangement tends to favor the recovery of o-xylene at the bottom by converting mixed xylenes in the column into additional o-xylene.

Preferably the single zone 26 of catalyst is disposed at the top, or within the upper half, of the fractionation column 10 which, in the example of FIG. 2, is the left-most of two physical towers.

As in FIG. 1, through the action of fractional distillation the o-xylene and $C_{9+}$ hydrocarbons will tend to migrate toward the bottom of the column as liquids. Therefore, regardless of the proportion of o-xylene in the feed to the xylene splitter column, the fractional distillation that occurs below the catalyst zone (where the feed is located) will remove o-xylene from the stream, enhancing its collection at the bottom of the column.

The p-xylene, m-xylene, and lighter hydrocarbons will tend to rise through the catalyst zone to an optional fractional distillation region above the catalyst zone. During passage through the catalyst zone, yet additional o-xylene will be created by the catalyst as it isomerizes the xylenes toward equilibrium. This creation of additional o-xylene in the catalyst zone enhances the collection of o-xylene at the bottom of the column.

The trays between the catalyst zone and the bottom of the column remove the lighter p-xylene and m-xylene to purify the o-xylene. When these lighter xylenes reach the isomerization catalyst, they become the source for the generation by isomerization of additional o-xylene for collection at the bottom of the column.

The optional fractional distillation region is shown having trays both below and above the level of a sidedraw 28. The trays below the level of the sidedraw have the effect of removing additional o-xylene, which tends to migrate downwardly. The trays above the sidedraw remove benzene and lighter products that are expected to be produced at least in small quantities by the isomerization catalyst. Hydrogen might also be present. These lighter products are removed as overhead and recycled. The stream that is produced by the sidedraw, which is beneficially enriched in p-xylene, is fed to the p-xylene recovery unit 16.

Figure 3:
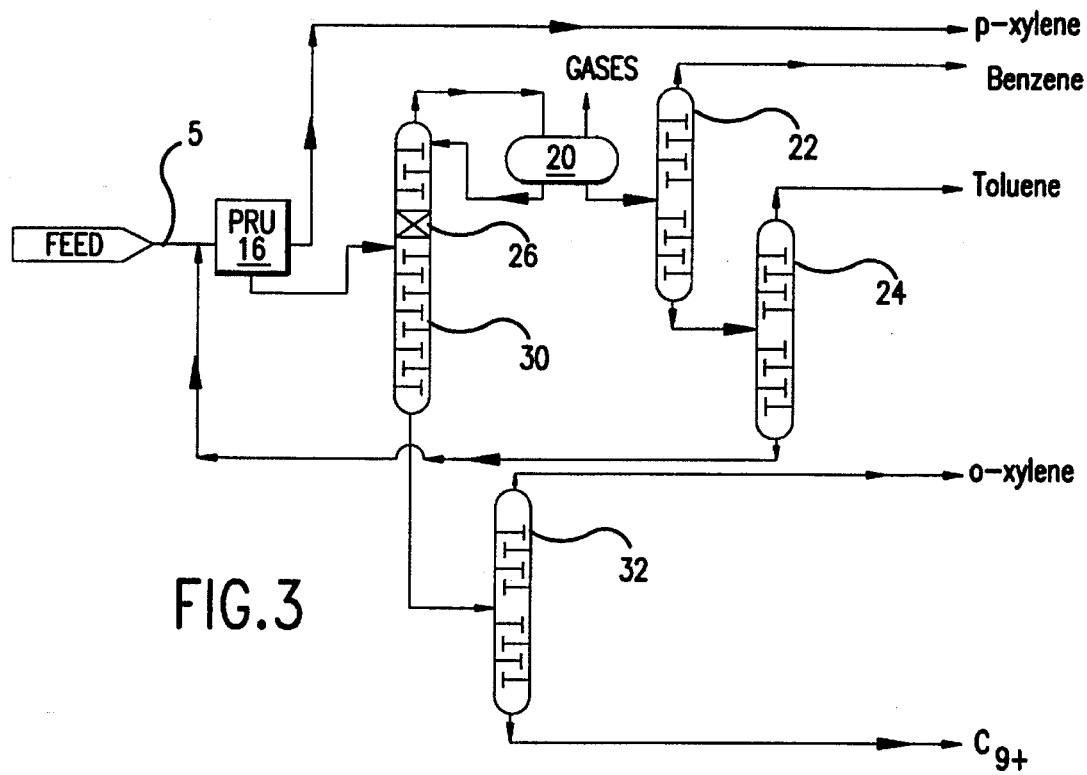
FIG. 3 shows a system specifically designed to carry out a modified form of a method according to the current invention and in which feed to a combined isomerization reactor/xylene splitter enters beneath a single zone of isomerization catalyst.

FIG. 3 shows an additional embodiment of apparatus for carrying out a process according to the current invention. This embodiment combines into one primary column 30 the functions that are performed by plural units in FIGS. 1 and 2. Therefore, it can have lower capital cost and is a candidate for new construction.

According to the process of FIG. 3, mixed xylene feed 5 is desirably introduced just upstream of a p-xylene recovery unit 16 of a known type. In the alternative, the mixed xylene feed may be introduced directly into the primary column 30, which will be described below. In the p-xylene recovery unit, p-xylene is recovered as a valuable product. The remaining stream, now enriched in o-xylene, is fed to the primary fractional distillation column that is, in effect, a combined primary isomerization reactor and xylene splitter.

The primary column 30 is provided with a single zone 26 of a catalyst effective to isomerize xylenes toward an equilibrium condition. The catalyst zone is located above the location of the feed. This arrangement tends to favor the recovery of o-xylene at the bottom by converting mixed xylenes in the primary column into additional o-xylene.

Preferably the single zone of catalyst is disposed at the top, or within the upper half, of the primary column.

As in the example of FIG. 2, through the action of fractional distillation the o-xylene and $C_{9+}$ hydrocarbons will tend to migrate toward the bottom of the primary column as liquids. Therefore, regardless of the proportion of o-xylene in the feed to the primary column, the fractional distillation that occurs below the catalyst zone (where the feed is located) will remove o-xylene from the stream, enhancing its collection at the bottom.

The bottoms of the primary column are fed to a fractional distillation column 32 where the o-xylene is separated from the $C_{9+}$ and is recovered as overhead.

In the primary column, the p-xylene, m-xylene, and lighter hydrocarbons will tend to rise through the catalyst zone 26 to a fractional distillation region above the catalyst zone. During passage through the catalyst zone, yet additional o-xylene will be created by the catalyst as it isomerizes the xylenes toward equilibrium. This creation of additional o-xylene in the catalyst zone enhances the collection of o-xylene at the bottom of the column. Furthermore, valuable p-xylene will be produced in quantity from the stream, from which p-xylene has been removed in the p-xylene recovery unit.

The trays between the catalyst zone and the bottom of the column remove the lighter p-xylene and m-xylene to purify the o-xylene. When these lighter xylenes reach the isomerization catalyst, they become the source for the generation by isomerization of additional o-xylene for collection at the bottom of the column.

The trays above the catalyst zone have the effect of removing additional o-xylene, which tends to migrate downwardly. The remaining xylene isomers and lighter products are removed as overhead and recycled in a conventional light ends recovery process.

In particular, gases are removed in a flash drum 20, from which reflux 34 is recycled back to the overhead of the primary column. The output of the flash drum is fed to a fractionation column 22 where benzene is recovered as overhead and $C_{7+}$ drawn off as bottoms. The $C_{7+}$ is fed to another fractionation column 24 where toluene is recovered as overhead and $C_{8+}$ is recovered as bottoms. The recovered $C_{8+}$ will include the p-xylene formed by isomerization in the primary column. This p-xylene is then recovered in the p-xylene recovery unit 16, and the process repeats.

Figure 4:
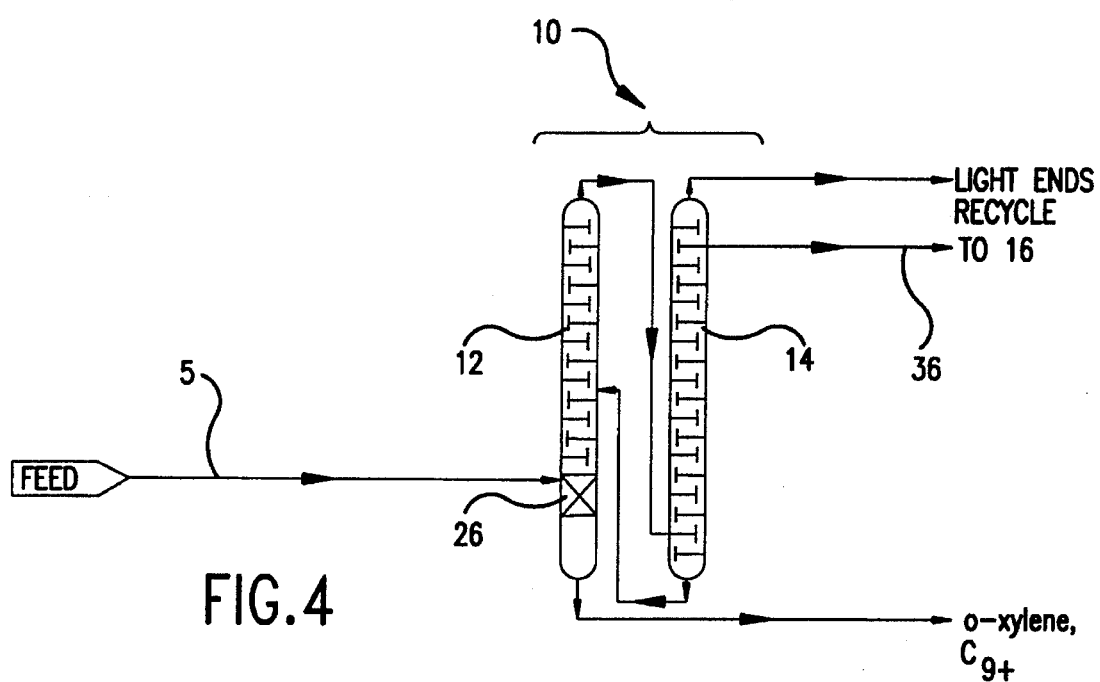
FIG. 4 shows a xylene splitter suitable for use in a system for carrying out a method according to the current invention in which feed to the xylene splitter enters above a single zone of isomerization catalyst.

The arrangement of FIG. 4 tends to favor the recovery of p-xylene near the top by converting mixed xylenes in the column into additional p-xylene. The figure shows a two-tower xylene splitter 10 similar to that shown in FIG. 2. Indeed, this form of apparatus could be substituted into the apparatus of FIG. 2 with the changes to be described below.

The xylene splitter 10 of FIG. 4 is provided with a single zone 26 of a catalyst effective to isomerize xylenes toward an equilibrium condition. The mixed xylene feed 5 is located above the location of the catalyst zone.

Preferably the single zone of catalyst is disposed within the lower half of the fractionation column which, in the example of FIG. 4, is the left-most of two physical towers.

Through the action of fractional distillation the p-xylene, m-xylene, and lighter hydrocarbons will tend to rise through the xylene splitter, and the o-xylene and $C_{9+}$ hydrocarbons will tend to pass to the bottom. The trays between the catalyst zone and the top of the column remove additional amounts of the heavier aromatics including o-xylene to further purify the p-xylene. A stream 36 enriched in p-xylene and m-xylene exits the xylene splitter near the top, while the light ends are removed as overhead for recycling, as in previous figures.

Also through the action of fractional distillation the o-xylene and $C_{9+}$ hydrocarbons will tend to migrate toward the bottom of the column as liquids, from which the $C_{9+}$ may be purged by subsequent distillation. If desired, the resulting xylenes may be purged from the system for use as solvents or fuels, or they may be combined with the recycle stream from the p-xylene recovery unit and recycled to the subject column or to another isomerization reactor. Ultimately the xylenes will enter isomerization catalyst, which will isomerize the mixture toward equilibrium. Therefore, regardless of the proportion of p-xylene in the feed to the xylene splitter column, the isomerization that occurs in the catalyst zone below the feed will create additional p-xylene. That enhances the recovery of p-xylene that ultimately will occur in the p-xylene recovery unit.

Figure 5:
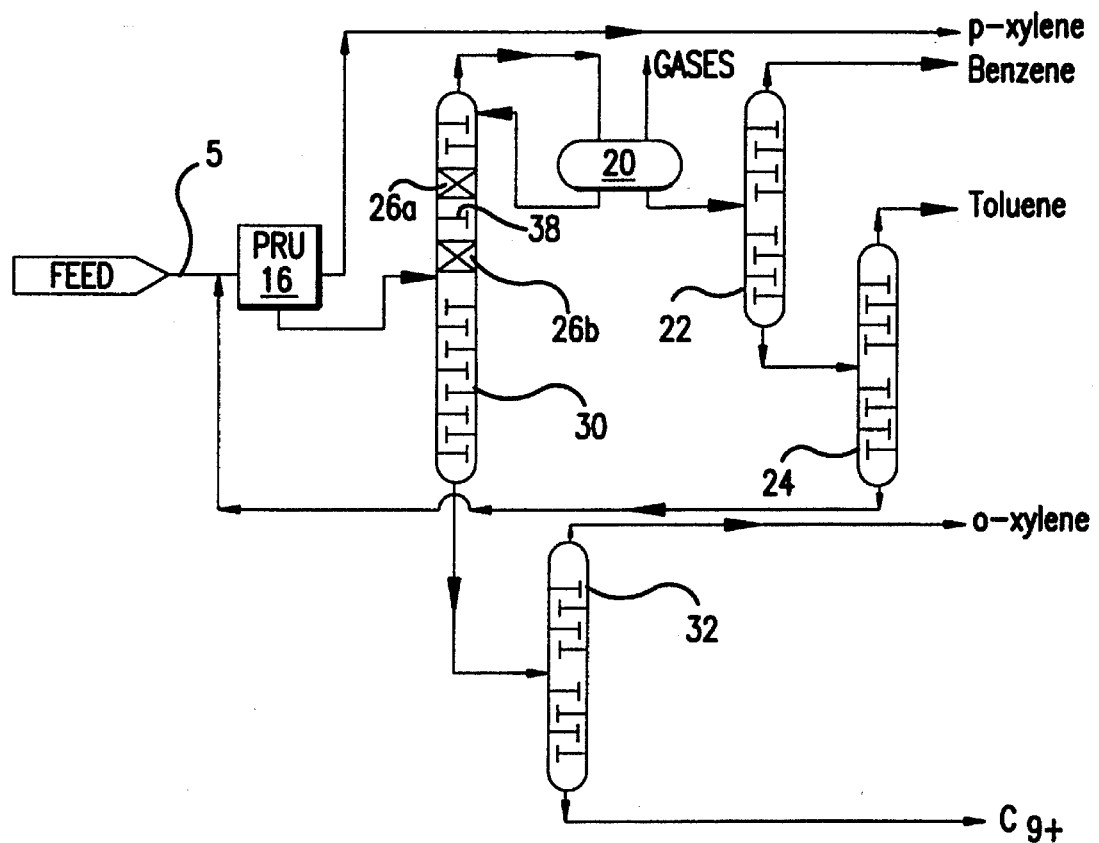
FIG. 5 shows a system specifically designed to carry out a method according to the current invention and in which feed to a combined isomerization reactor/xylene splitter enters between two zones of isomerization catalyst and in which fractional distillation is carried out between the two zones of catalyst.

FIG. 5 shows an additional embodiment of apparatus for carrying out a process according to the current invention. Like FIG. 3, this embodiment combines into one primary column 30 the functions that are performed by plural units in FIG. 2. Therefore, it can have lower capital cost and is a candidate for new construction.

According to the process of FIG. 5, mixed xylene feed 5 is desirably introduced just upstream of a p-xylene recovery unit 16 of known type. In the alternative, the mixed xylene feed may be introduced directly into the primary column 30, which will be described below. In the p-xylene recovery unit, p-xylene is recovered as a valuable product. The remaining stream, now depleted in p-xylene, is fed to the primary fractional distillation column that is, in effect, a combined primary isomerization reactor and xylene splitter.

The primary column is provided with two zones 26a, 26b of catalyst effective to isomerize xylenes toward an equilibrium condition. The feed is located between the two catalyst zones.

It may be desirable to subject the feed to fractional distillation between the zones of isomerization catalyst to alter the reaction conditions. Different catalyst media might be used in each zone to effect a different reaction. An example is an ethylbenzene cracking catalyst in the upper zone and an ethylbenzene isomerization catalyst in a lower zone. For this purpose, FIG. 5 shows trays 38 between the zones.

The bottoms of the primary column are fed to a fractional distillation column 32 where the o-xylene is separated from the $C_{9+}$ and is recovered as overhead. The remaining xylene isomers and lighter products are removed as overhead and recycled in a conventional light ends recovery process.

In particular, gases are removed in a flash drum 20, from which reflux 34 is recycled back to the overhead of the primary column 30. The output of the flash drum is fed to a fractionation column 22 where benzene is recovered as overhead and $C_{7+}$ drawn off as bottoms. The $C_{7+}$ is fed to another fractionation column 24 where toluene is recovered as overhead and $C_{8+}$ is recovered as bottoms. The recovered $C_{8+}$ will include the p-xylene formed by isomerization in the primary column. This p-xylene is then recovered in the p-xylene recovery unit, and the process repeats.

In view of the above, it may be seen that the invention broadly contemplates the improvement of known processes involving catalytic isomerization and fractional distillation for the recovery of o-xylene or p-xylene wherein the improvement comprises the steps of contacting mixed xylenes in a fractionation column with an isomerization catalyst, thereby isomerizing $C_8$ aromatic hydrocarbons in the fractionation column toward equilibrium and consequently enhancing the effectiveness of the fractional distillation in the recovery of o-xylene or p-xylene or both.

In each variation of the process described, ethylbenzene may be present in the mixed xylene feed. The process can be carried out whether or not ethylbenzene is present. If present, depending on the catalyst system, it will be cracked to benzene or isomerized into additional xylenes.

Also, each variation of the process can be carried out at part of either of the two main classes of xylene isomerization reactions discussed above in the "Discussion of the Background." These are: 1) the class in which all four of the $C_8$ aromatic isomers are isomerized toward an equilibrium mixture, and 2) the class in which only the xylenes are isomerized toward an equilibrium mixture; the ethylbenzene is converted into benzene.

The following Example will serve to illustrate a specific embodiment of apparatus for carrying out the process disclosed herein. This example should not, however, be construed as limiting the scope of the novel invention contained herein, as there are many variations which may be made thereon without departing from the spirit of the disclosed invention, as those of skill in the art will recognize.

EXAMPLE

A glass column having a diameter of 3 inches, a height of 24 feet, and a closed top was fitted with a kettle reboiler (pot)

at the bottom. The column was filled for a distance of 18 feet with Goodloe® mesh-type packing supplied by Otto H. York Company. Above the packing, the column was filled for a distance of 6 feet with 0.3 cubic feet of high-activity isomerization catalyst supplied by Engelhard Corporation. Between the catalyst and the closed top was a water-cooled condenser.

The column was charged with mixed xylenes as described in Table 1, and the pot temperature was slowly increased during the course of the run until the reaction temperature at the catalyst reached a steady state at approximately 139 degrees C. The interior of the column remained substantially at atmospheric pressure throughout the run. After approximately ten hours of total reflux the reaction products were removed and analyzed. The results are given in Table 1.

TABLE 1

|  | (percent by weight) | | | |
| --- | --- | --- | --- | --- |
|  | o-xylene | p-xylene | m-xylene | ethyl-benzene |
| Feedstock | 15.17 | 22.41 | 51.52 | 10.53 |
| Equilibrium Value[1] | 17.6 | 24.0 | 56.9 | 2.3 |
| Reaction Products | 19.24 | 20.09 | 54.31 | 6.36 |

[1]Equilibrium values estimated from commercially-available sources for the four-isomer system at 139 degrees C.

As shown in Table 1, the concentration of o-xylene increased above its equilibrium value during this total reflux test. The p-xylene concentration moved away from its equilibrium value, and the concentrations of the other constituents moved toward their equilibrium values. Therefore, it can be concluded that contacting the contents of the fractionation column with an isomerization catalyst, thereby isomerizing $C_8$ aromatic hydrocarbons in the fractionation column toward equilibrium, consequently enhanced the effectiveness of the fractional distillation in the recovery of o-xylene or p-xylene.

A latitude of modification, change and substitution is intended in the foregoing disclosure and in some instances some features of the invention will be used without a corresponding use of other features. Accordingly, it is appropriate that the appended claims be construed broadly and in a manner consistent with the scope of the invention therein.

What is claimed is:

1. In a process in which hydrocarbons including $C_8$ aromatic hydrocarbons are treated to recover a desired isomer of xylene, wherein the process comprises the steps of receiving a mixture that contains mixed xylenes into a fractionation column, subjecting said mixture to fractional distillation in the fractionation column, and drawing a stream rich in said desired isomer from the fractionation column, the improvement comprising the steps of:

contacting contents of the fractionation column with an isomerization catalyst, thereby isomerizing $C_8$ aromatic hydrocarbons in the fractionation column toward an equilibrium mixture of isomers, producing more of the desired isomer and consequently enhancing the effectiveness of the fractional distillation in the recovery of said desired isomer.

2. The process of claim 1, wherein the isomerization catalyst is disposed at a single zone within the fractionation column, and the receiving step comprises receiving the mixture into the fractionation column at a location beneath the isomerization catalyst.

3. The process of claim 1, wherein the isomerization catalyst is disposed at a single zone within the upper half of the fractionation column, and the receiving step comprises receiving the mixture into the fractionation column at a location beneath the isomerization catalyst.

4. The process of claim 1, wherein the isomerization catalyst is disposed at a single zone within the fractionation column, and the receiving step comprises receiving the mixture into the fractionation column at a location above the isomerization catalyst.

5. The process of claim 1, wherein the isomerization catalyst is disposed at a single zone within the lower half of the fractionation column, and the receiving step comprises receiving the mixture into the fractionation column at a location above the isomerization catalyst.

6. The process of claim 1, wherein the isomerization catalyst is disposed in two zones within the fractionation column, and the receiving step comprises receiving the mixture into the fractionation column at a location between the two zones.

7. The process of claim 6, including the step of subjecting the mixture to fractional distillation between the two zones of isomerization catalyst.

\* \* \* \* \*